(12) United States Patent
Gregersen

(10) Patent No.: US 6,821,484 B1
(45) Date of Patent: Nov. 23, 2004

(54) APPARATUS FOR ISOLATION OF PARTICLES, PREFERABLY CELL CLUSTERS

(75) Inventor: Soeren Gregersen, Lystrup (DK)

(73) Assignee: Accip Biotech APS, Arhus (DK)

( * ) Notice: Subject to any disclaimer, the term of this patent is extended or adjusted under 35 U.S.C. 154(b) by 0 days.

(21) Appl. No.: 09/786,495

(22) PCT Filed: Sep. 1, 1999

(86) PCT No.: PCT/DK99/00458
§ 371 (c)(1),
(2), (4) Date: Apr. 30, 2001

(87) PCT Pub. No.: WO00/13609
PCT Pub. Date: Mar. 16, 2000

(30) Foreign Application Priority Data

Sep. 2, 1998 (DK) .......................................... 1998 01102

(51) Int. Cl.⁷ ............................. G01N 35/00; G06K 9/20
(52) U.S. Cl. .......................... 422/73; 422/100; 422/101; 422/103; 422/63; 422/67; 436/43; 436/54; 436/177; 436/180; 382/128; 382/133
(58) Field of Search ...................... 422/68.1, 73, 82.05, 422/100, 101, 103, 922, 924, 63, 67; 436/10, 43, 49, 54, 164, 177, 180; 382/128, 133

(56) References Cited

U.S. PATENT DOCUMENTS 4,965,725 A  10/1990  Rutenberg
5,073,857 A  12/1991  Peters et al.
5,106,584 A  * 4/1992  Funakubo et al. ............. 422/65
5,848,177 A  12/1998  Bauer et al.
6,146,881 A  * 11/2000  Hering ..................... 435/284.1

FOREIGN PATENT DOCUMENTS

EP      0195088      9/1986
EP      0336608      10/1989
WO      WO99/08091   2/1999

OTHER PUBLICATIONS

Patent Abstracts of Japan, App. No. 04261946—Tadashi.

Patent Abstracts of Japan, App. No. 61097185—Katsuya.

Patent Abstracts of Japan, App. No. 08147127—Koji.

* cited by examiner

Primary Examiner—Maureen M. Wallenhorst
(74) Attorney, Agent, or Firm—Klein, O'Neill & Singh, LLP; Howard J. Klein

(57) ABSTRACT

An apparatus for the isolation of cell clusters that are either embedded or transported is preferably used for the isolation of the insulin-producing pancreatic islets of Langerhans, but it also can be used for the isolation of other types of cell clusters and particles in fluids as well. The apparatus employs digital imaging of the cell suspension on either a plane surface or in a capillary tubing, wherein a digital camera scans the cell suspension.

9 Claims, 7 Drawing Sheets

APPARATUS FOR ISOLATION OF PARTICLES, PREFERABLY CELL CLUSTERS

FIELD OF THE INVENTION

The invention relates to the field of isolating cell clusters from a tissue suspension with the special aim of isolating islets of Langerhans.

BACKGROUND OF THE INVENTION

Diabetes is characterized by a defect in the insulin producing beta-cells in the pancreas. The beta-cells are localized in the islets of Langerhans surrounded by exocrine tissue. The responsiveness of the beta-cells to extracellular glucose is essential for a normal glucose homeostasis. There is a great need for isolated islets from both animals and humans for several purposes: 1. Research on basal physiological and pathophysiological mechanisms in the endocrine pancreas, 2. Screening and testing of insulinotropic, potential antidiabetic drugs and 3. allo- and xeno-transplantation of islets. The efforts put into clinical islet transplantation is greatly curtailed by the problems in isolating an adequate islet mass for reducing the diabetic state. The islet harvesting process involves principally two different stages, one is the collagenase digestion of the exocrine- and connective tissue and the second is the separation of the islets from the dispersed tissue suspension. The collagenase digestion technique has been known for many years and involves either injection of collagenase (or another dissociating agent) into the duct system of the pancreas or treatment of small pieces of pancreas with collagenase (Lacy & Kostianovsky, 1967). The tissue disintegrates hereby.

Subsequently to tissue digestion, several different methods can be used for separating the islets from the exocrine tissue. These include, among others, 1). manual picking of the islets or sucking the islets into a pipette, 2). serial siewing procedures, 3). laminar flow channels, 4). density-gradients, 5). cell separators. Combinations of these methods have also been reported.

Concerning isolation of islets from smaller animals manual picking of islets is very common. This method is time-consuming and the extended periods used for the isolation may be detrimental for studies on e.g. molecular biology of the islets. In addition, the method involves monotonous and sedentary work. This demanding work is often done by laboratory technicians, students, MDs etc (depending on resources and local tradition).

The time spent on islet isolation can be utilized much more efficiently and/or salary expenses can be reduced greatly by automation. In addition, it is well known that sedentary, monotonous work is related to an increased number of days lost through sickness (e.g. as a cause of pain in the neck- and shoulder-region, headache etc). Other important disadvantages of manual picking of islets are clear: the risk of differences in the handling and selection of the islets by different operators (common to all methods). This can cause a large variation in the measured biological parameters. Clearly, also the time-factor is of importance since it is generally accepted that fast transfer of the islets to an optimal culture-medium prevents damage to the islets.

There has been a general lack of standardization and quality measures of the isolation process, especially within the area of human islet isolation (see (Ricordi, 1991)) despite the fact that in order to improve the isolation process it is imperative to document in detail differences in islet yield and quality.

It is of great importance to develop methods for large-scale and fast automated isolation of islets from both animals and humans and some efforts have been put into this area. It is however evident that none of the previously presented methods have been neither widely accepted nor widely used. This counts especially for the area of animal islet isolation.

In contrast, within the area of human and pig islet isolation the development of automated methods for isolation of islets have greatly improved the outcome. Thus, the well-known automated islet isolator (AII) as developed by Ricordi et al. (Ricordi, Lacy, et al.1988, Ricordi, Finke, et al. 1986) and modifications hereof (Teruya, Idezuki, et al. 1994, Lakey, Warnock, et al. 1997) has enabled clinical and experimental transplantation of islets for treatment of human diabetes. Ricordis method combines collagenase digestion with a device for separation of the islets in the same apparatus. The islets are continuously released from the tissue when it is degraded.

However, the Ricordi method requires additional purification by gradient centrifugation (Ricordi, Finke, et al. 1986, Ricordi Lacy, et al. 1988, Ricordi, Finke, et al. 1988). It may also result in variations in the time the islets are treated with collagenase and thus produce islets with varying quality and characteristics. It may not be advantageous to combine the digestion process with the separation process in the same apparatus.

Several other methods have been developed, e.g. density gradient centrifugation for isolation of human islets and for isolation of islets from rodents dogs, pigs and humans (Marchetti Finke, et al. 1991, Tze, Wong, et al. 1976, Ricordi, Lacy, et al. 1988, Shibata, Ludvigsen, et al. 1976, Buitrago, Gylfe, et al. 1977). A few laboratories combines gradient centrifugation with a cell separator (Lake, Basset, et al. 1989, Olack, Swanson, et al. 1991, Prevost, Rolland, et al. 1995). The use of gradients can be gravely criticized since these may cause osmotic damage to the islet cells (Lake, James, et al. 1986, Lake, Anderson, et al. 1987). Potentially, this could be of great importance for the outcome of islet transplantation. In addition, the purity reported using these methods varies greatly and often is around 75%. It would be of great advantage to increase the purity of the isolate.

Other methods for digestion/separation of islets have been described (see for example (Brunicardi, Suh, et al. 1992, Gray & Baird 1996)), e.g. immunomagnetic isolation (Nandigala, Chen, et al. 1997, Davies, James, et al. 1995) and fluorescence activated cell sorting (FACS) of islets marked with e.g. zinc binding dye (Jindal, McShane, et al. 1994) or neutral red (Gray, Gohde, et al. 1989). Laminar flow channels (Langley. 1993) and filtering of the digested tissue (Sharp, Lacy, et al. 1986) for purification of islets have also been developed. Siewing of tissue preparations is commonly used as a rough, first-line method for getting rid of large undigested tissue pieces.

It is obvious that within the area of animal islet research none of these methods are widely used and the manual islet isolation is still very common and used by most laboratories including those in the pharmaceutical industry. It is clear, therefore, that efforts should be put into facilitation of isolation process since substantial resources are used on this process. In addition, advantages are increased quality of the isolated products and the invention will also reduce inter-operator variation in selection of islets. Improved methods for isolation of rodent islets are useful for the research regarding transplantation and improved methods in this are likely to rub off on the human islet transplantation.

It is an object of the present invention to substantially improve the isolation process. It takes advantage of, and incorporates improvements, of the conventional methods for disintegration of the tissue of interest. It may be used for primary isolation of islets from the surrounding tissue but may also be used for later purification or transfer of islets from one place to another. The primary goal is to provide a fast, reliable apparatus for isolation of pancreatic islets of Langerhans and in the same apparatus implement documentation.

SUMMARY OF THE INVENTION

The invention is concerned with isolation of cell clusters embedded in a tissue suspensign. The apparatus is preferably designed for isolation of pancreatic islets but is applicable to many kinds of cell clusters, single cells, for example spermatozoa, or non biological particles. It takes advantage of conventional methods for disintegration of the primary tissue containing the cell clusters of interest. The principle of the invention is that the apparatus automatically detects the cell clusters in the tissue suspension and subsequently isolate and transfers them to another location. The detection of the cell clusters is carried out by digital image processing followed by isolation by means of either a moving pipette or performed in a capillary tubing.

DETAILED DESCRIPTION OF THE INVENTION

Figure 1:
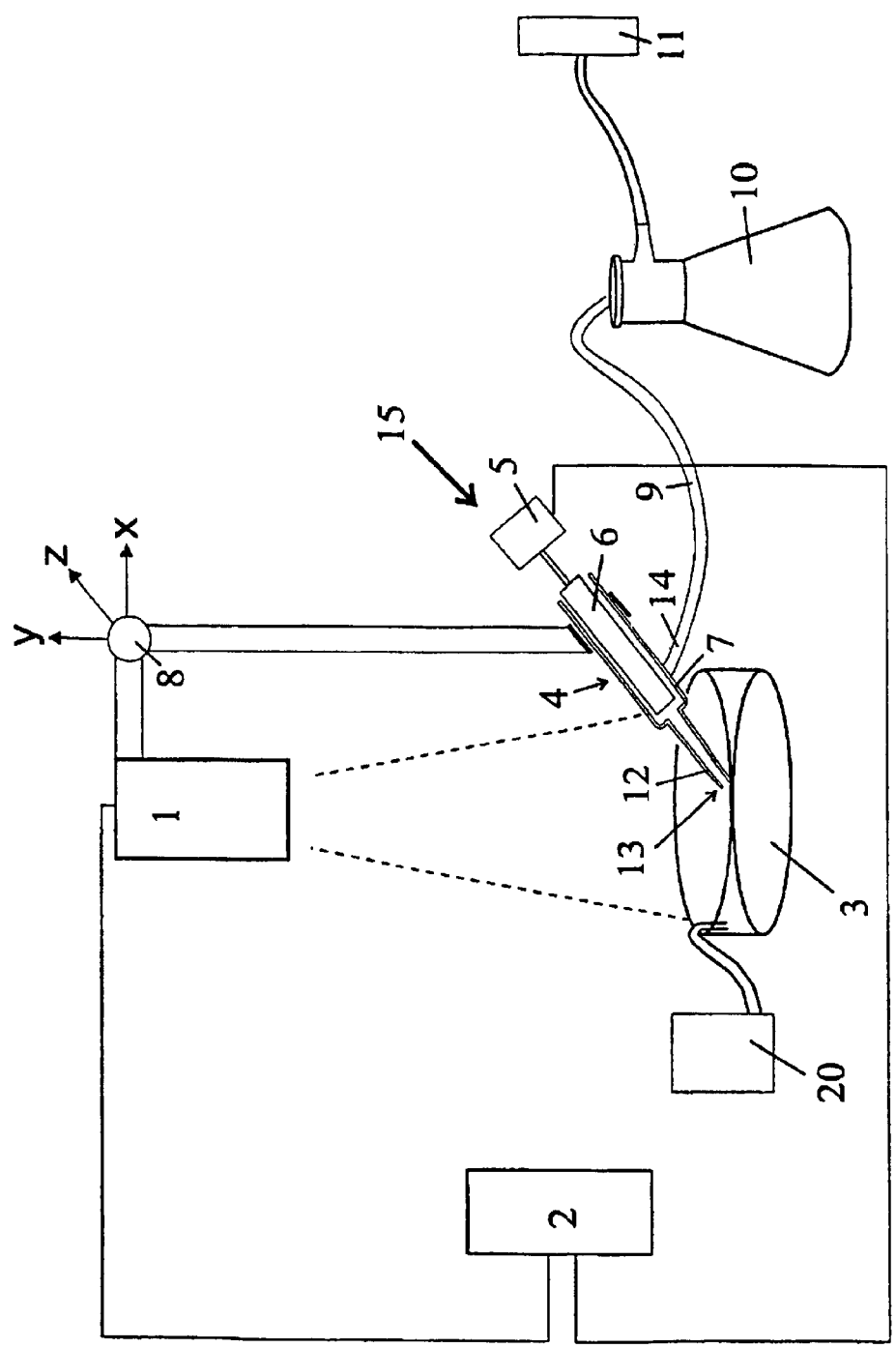
FIG. 1. Apparatus I in schematic form.

The invention is designed with the specific aim of isolation of islets of Langerhans and specifically for separation of rodent islets. However, the invented apparatus can be used for other cell clusters, single cells or non-biological particles as well. In the following the apparatus will be described by an example of particles, which are islets of Langerhans It is emphasized, that the apparatus can be used within many fields of biomedical research and development. Regarding the field of islet research, this may include e.g. basal islet research (secretion, molecular biology), screening of pharmaceuticals, islet transplantation, isolation of re-aggregated islet cells (e.g. artificial islets/pseudoislets), isolation of genetically modified islets or islet cell clusters. The apparatus can be used also for isolation of human islets and the flexibility of the software is clear since it provides means of easily learning the program the characteristic features of islets from different species. Human islets are used both within basal research (including drug development) and in particular for islet transplantation. The invention may also be used within other biomedical research areas: isolation of cells/cell clusters from enzymatically disintegrated organs, e.g. thyroid and parathyroid, from animals and humans (cf. ref. (Loir 1988)), isolation of anti-body conjugated cells (e.g. erythrocytes, (Lubbe, Rossi, et al. 1976)) and in broader words identification, isolation and/or transfer of any kind of cell or cell clusters identifiable and processable by the apparatus. Herein is included single cells as spermatozoa and egg cells. The apparatus is also applicable for investigations including cell clusters originating from single cell organisms including bacteria, clusters of viruses, cells conjugated or aggregated to form cell clusters initiated by antibody or any other biological or non-biological substances.

The invention is based on fulfilment of the following important demands to an optimal isolation process:

A. It is of outmost importance that the islets are not damaged in any way—physically or chemically—during the isolation process. This is of particular relevance when isolating fragile islets such as porcine islets (Prevost, Rolland, et al. 1995). Thus, the apparatus is capable of detecting and isolating the islets without the use of color or antibodies and without the exposure to gradients, centrifugal forces, magnetic fields, etc. This ensures that the integrity of the islets remains intact The pipette systems proposed here allows the researcher to choose a particulate pipette for a special purpose to ensure the safe isolation of the islets.

B. Efficiency and purity: fast isolation and a high degree of purity is secured by both apparatus invented. In contrast to all other methods and apparatus known from literature these apparatus will produce a purification percentage close to 100 due to the special construction. This is of particular interest in islet transplantation where it may protect against rejection.

C. It is important that the islets are isolated fast securing quick removal from the original tissue suspension and transfer to conditions more suitable for survival of the cells (e.g. fresh culture medium). It is generally accepted that it is preferable to perform fast isolation of the islets after the collagenase treatment for at least two reasons: 1. residual collagenase may still be in solution and 2. substances (e.g. cytokines and enzymes) present in the tissue suspension may be detrimental to the islets.

D. The isolation should be performed under conditions protecting from damage to the cells (e.g. at low temperature and at sterile/semi-sterile conditions). Thus, the apparatus can be placed either in a refrigerated room (4° C.) or the parts supporting the petri dish can be cooled. The risk of contamination is reduced since pipettes, tubes, etc., can be autoclaved (or single-use).

E. Standards for good laboratory practice should be fulfilled: Using Digital Imaging physical parameters (size, shape, volume) can be measured easily. This gives one the opportunity to perform daily quality controls and thereby the collagenase digestion can easily be optimized based on true objective criteria. Adequate documentation can help the process of reaching an international consensus on standards for measuring the size and quality of islets, e.g. number of islet equivalents (IEQ) (Ricordi, Gray, et al. 1990, Vandewalle, Douillard, et al. 1999). Standardization and documentation of the procedure is also in good agreement with the concept 'Good Laboratory Practice' (GLP). Digital Image Analysis has previously shown high correlations with computer assessed volume determinations and independent quantity parameters such as DNA and insulin contents (Stegemann, O'Neil, et al. 1997, Stegemann, O'Neil, et al. 1998).

F. Economy: The expenses used for isolation of one islet should be kept to a minimum without compromising the quality of the isolated islets. The use of the invention will save time and money since the processing will require minimal operator manipulation. This enables more efficient use of time for scientific personnel and laboratory technicians, a reduction in monotonous routine work and thus be expected to reduce the number of days lost through sickness G. Improvement of the working conditions based on automation of the process.

H. Additional aspects: The fact that the isolation process and the quality-control is combined in one unit saves time. It is to be expected that a higher quality of the islets will result in a higher success rate of the experiments performed. In the long run this will result in a reduced number of animals needed for the experiments.

The invention will combine low cost with efficacy and high quality of the outcome, the isolated islets. To document the effectiveness of the invention with regard to the latter of these parameters, the integrity of the isolated islets should be similar to, or even better, than islets isolated by traditional methods. This includes measures of secretion and physical parameters (Vandewalle, Douillard, et al. 1999).

Digital Imaging has been used for describing physical characteristics of the islets (e.g. counting and size) (Stegemann, O'Neil, et al. 1997, Stegemann, O'Neil, et al. 1998, Merchant, Diller, et al. 1996, Fetterhoff, Wile, et al. 1994, Wile, Schwartzkopf, et al. 1997) but the step to use the method for isolation of the islets has not been taken.

The basis for the invention is the use of conventional methods for tissue disintegration. The apparatus according to the invention is particularly useful for tissue treated with enzymatic solutions such as collagenase and/or trypsin leaving the cell clusters in the tissue suspension from which they are to be isolated. However, any kind of dissociating substance or method for producing the tissue suspension can be used and is therefore not limited to the use of enzymatic solutions attacking the tissue.

For clarification, a method for disintegration of the rodent pancreas into a tissue suspension containing islets of Langerhans is described here since this is the preferred embodiment. In brief, the common bile duct of the rodent pancreas is ligated at the papilla Vateri, where after the hepatic duct is cannulated and ice-cold Hanks Balanced Salts Solution (HBSS) containing collagenase is injected into the duct system of the pancreas (Gotoh, Maki, et al. 1987). The inflated pancreas is removed and fat and vessels are trimmed off. The pancreas is placed in a test tube and kept on ice until incubation at 37° C. for 16.5–19 min. After 2×5 seconds of vortexing, the tissue solution is washed with ice-cold HBSS. Eventually, the tissue suspension is hereafter siewed on a nylon mesh to extract non-degraded tissue, fat, vessels etc. (Hara, Taniguchi, et al. 1988). The siewing of the tissue is a preferable, but not necessary, step as preparation of the tissue suspension before subjecting it to an isolation process as the one described here. Siewing of tissue preparations is commonly used as a rough, first-line method for getting rid of large undigested tissue pieces. After the isolation of the islets these can be used immediately or they can be subjected to a recovery period before used in experiments or transplantation.

Two apparatus are outlined, I and II. Both solutions are based on photo detection of the islets (digital imaging) in a capillary tube device. In apparatus I, islets in suspension in a petri dish are sucked into a pipette and transported to a second container. In apparatus II, islets moving in a fluid inside a capillary tube are detected and separated.

Apparatus I ensures safe scanning before isolation and low contamination by non-islet tissue in the isolate. This apparatus is fast and depending on the pipette used it can be extended to transfer islets to e.g. multi-well or microtiter plates for immediate analysis or experiments. To ensure fast, reliable isolation with a minimum of contamination, pipettes suited for the apparatus have been developed and are described below. The flow-through pipette (see below) speeds up the isolation process greatly since the pipette tip remains in the fluid of the petri dish at all times. It also ensure full use of the software features outlined below.

Apparatus II enables quick isolation of the islets transported in the capillary tubing and more than one capillary tubing can be placed under a single camera thus enabling high-speed isolation. In addition, this apparatus contains a minimum of mechanical parts and is mechanically very stable in the long run. However, this apparatus requires more data power than apparatus I due to the on-line scanning of the fast flowing tissue in the capillary tubings.

FIG. 1 shows the apparatus I in schematic form. The apparatus I, as outlined in claim 3, comprises a digital camera (b/w, or eventually color) or a line scan camera (1) coupled to a computer (2) with software for digital image analysis. The camera scans a first container, which is, for example, a petri dish (3) containing tissue suspension. The digital camera (1) is equipped with a zoom lens allowing the camera (1) to image areas of variable size, for example 1 cm×1 cm. The capillary tube device (15) for this model, as shown in FIG. 1, comprises a pipette (4) and a transport stage (8).

The camera (1) and the pipette (4) to pick up cell clusters from the suspension are in one embodiment of the invention moved together as one unit in the x-y-z plane by the transport stage (8). A computer-controlled electrical motor or piezo-unit (5) moves the piston (6) inside the pipette mantle (7). The transport stage makes it possible to move the pipette (4) around in the petri dish (3) by fast movements performed by for example computer-controlled electrical stepper motors or a commercially available x-y-z stage modified for this purpose.

In another embodiment of the invention, the pipette (4) and the camera (1) are not moved as one unit. In that case, the camera (1) is either moved by separate x-y movements or it is held in one position at all times.

The pipette tip (12) (capillary end section) is visible in the field of view of the camera (1). In one embodiment of the invention, a non-flow-through pipette is used (see model 1 explained below), where the pipette (4) after isolation of one or several islets is moved outside the petri dish (3) to expel the islets into a second container (10), for example a separate petri dish, a culturing flask, or microtiter plates.

In other embodiments of the invention (see the different models 2–4 described below), the pipette (4) is coupled via a transport tube (9) to a second container, for example a culture flask (10) containing culture medium. The principle of the pipette system (15) can be as indicated: in the culture flask (10) a small negative pressure is made by a suction device (11) so that the islets are moved from the dish (3) through the pipette (4) to the flask (10). The suction pressure in the transport tube (9) is controlled via one or more manometers.

After a petri dish has been emptied for islets, a new petri dish (3) is placed in the image field of the camera (1) and solution containing islets is fed from a reservoir (20) into the new petri dish (3). To maintain the solution level in the petri dish, additional solution can be added from a supply container (not shown).

To prevent clotting of the pipette system, cleaning routines are included in the software. The fast movements need to be performed with a precision that depends on the type and size of the cell clusters to be isolated, for example 0.05–0.1 mm.

After recognition of an islet, the pipette is moved into the vicinity of the islet and suction of suspension containing the islet into the pipette is started. As soon as the suction starts, the pipette is moved away from the islet, typically upwards, in order to suck only the islet into the pipette and not further tissue from the surroundings, which tissue is unwanted in the separation procedure.

Potentially, the equipment can be used for transfer of islets directly to incubations vials or well-plates.

Figure 2:
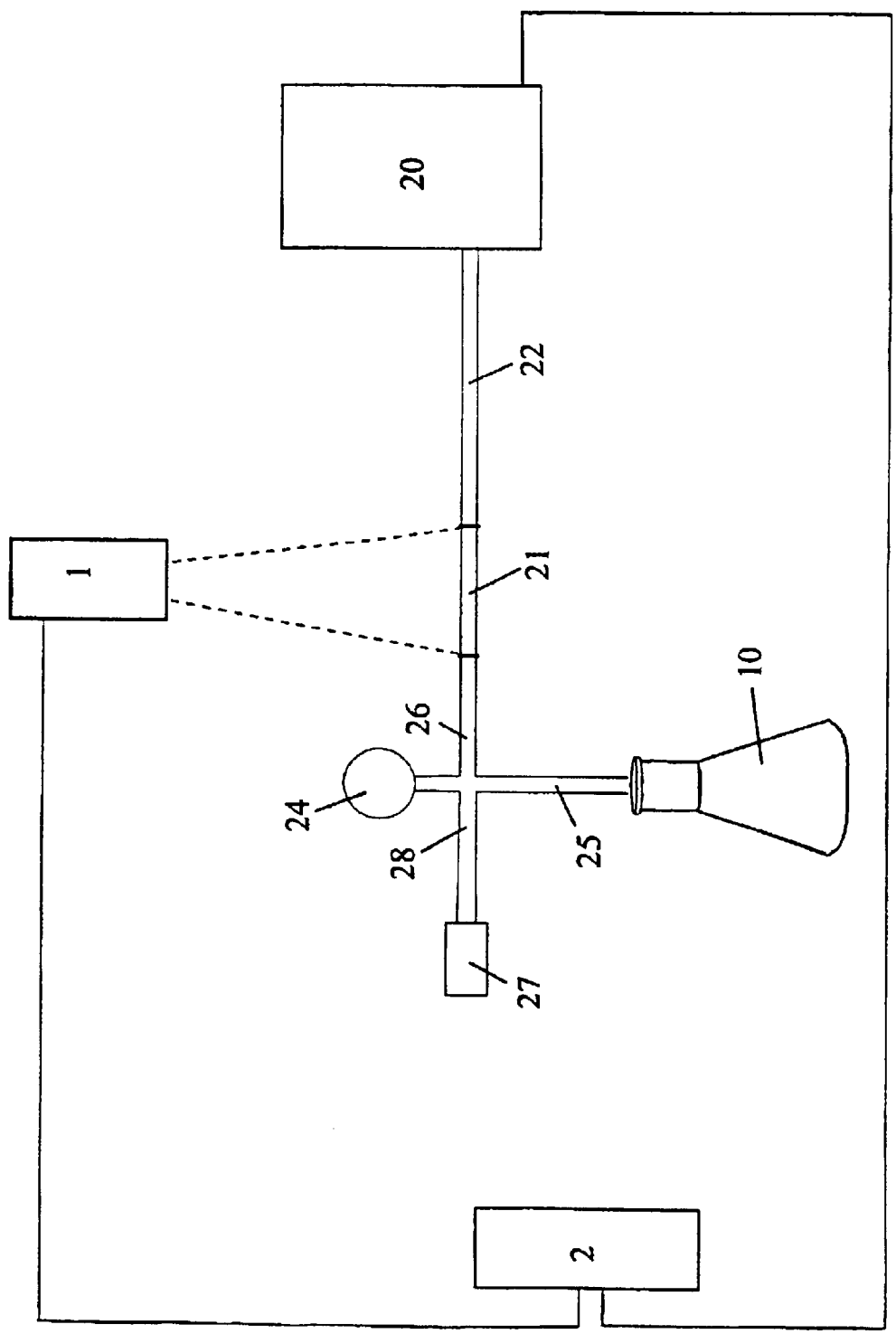
FIG. 2. Apparatus II in schematic form.

FIG. 2 shows apparatus II in schematic form. The apparatus II, as outlined in claim 2, comprises a digital camera (b/w, or eventually colour) (1) with a zoom lens, for example a full-field imaging camera or a line scan camera, which is connected to a computer (2) with the software for digital image analysis. The camera (1) scans a transparent section (21), for example a glass or plastic capillary, in the first container. The inner diameter or the transparent tube (21) is larger than the largest islets to be isolated; typical islet sizes are 0.1–0.35 mm. The length of the transparent section (21) is variable, for example 2–3 cm. The inner shape of the transparent tube (21) can be of different geometrical shapes in cross and longitudinal section, e.g. round, or quadratic. The transparent tube (21) is, via a the first transport section of first container (22), for example a silicone tubing, connected to the reservoir (20) containing the tissue suspension. The suspension flows from the reservoir (20), through first transport section of first container (22), the transparent section (21) and a second transport section of first container (26) into a further tube (28), which is connected either to a waste container (27), or back to the reservoir (20) for recirculation of the suspension.

When the islets in the transparent section (21) are detected by the computer program implemented in the computer (2), a micro-pump (24) (or a controlled valve) is activated by the computer program at the right moment, and a small liquid flow is created perpendicular to the second transport section of the first container (26), whereby the islet are directed into the side-tubing (25) instead of the further tube (28).

It is also possible to use a pipette system connected to the side tube (25) instead of a micropump (24) or valve, which pipette systems are explained in detail in FIGS. 3 through 6.

Potentially, the equipment can be used for transfer of islets directly to incubations vials or well-plates.

PIPETTES—EXAMPLES

The pipettes (4) for suction of the cell clusters are part of the invention. The type of pipette differs depending on the process and the tissue of interest. Thus, for the preferred embodiment, isolation of islets of Langerhans, the pipette designated model 3 (FIG. 5) is preferred, as it combines fast, non-hazardous, continuous transfer of the cell clusters without the risk of quickly depleting the petri dish of fluid. Furthermore, in combination with a fast z-movement of the pipette, it is possible to suck the islet into the pipette without transferring material other than the islet of interest. This is of importance for the purity of the suspension containing the isolated cells. It further secures that minimal disturbances occur in the vicinity (13) of the pipette tip (12) when the islets are isolated. Disturbances may hamper the identification by the camera and the computer program.

When developing the different types of pipettes (4), it was also of importance to reduce back-flow of fluid from the pipette (4) into the petri dish (3), which may happen when the piston (6) moves back to the first position, which is the position, where the piston is fully inserted into the pipette mantle. This problem is not present in model 4 (FIG. 6) and it is minimized in model 2 and 3 by the special construction enabling the fluid to pass through the outlet (30) (FIG. 4 and 5) instead of flowing out of the tip (12) when the piston (6) moves back to first position.

Figure 3:
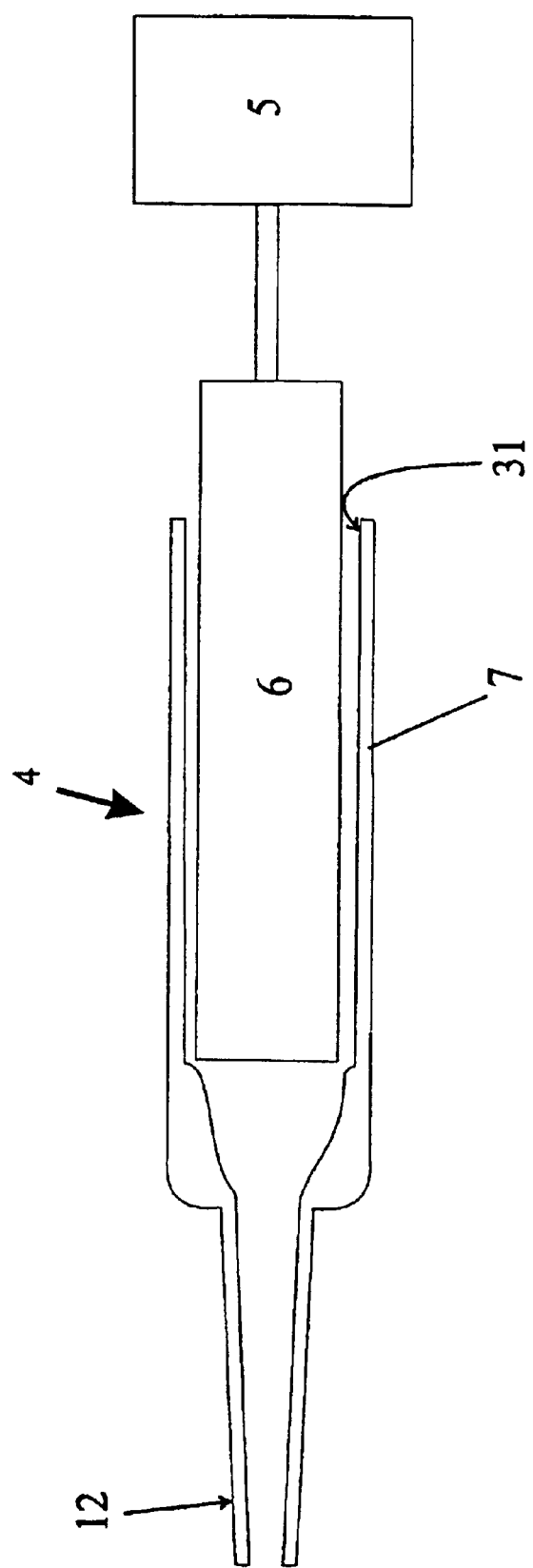
FIG. 3. Pipette model 1: Non-flow-through pipette.

FIG. 3 shows pipette model 1, which is a non-flow-through pipette. The material making op the pipette (4) per se can be glass, plastic, metal or a combination. In order not to disturb the camera field of view, a transparent material for the tip (12) is preferred. The pipette (4) can be made by founding of the entire pipette mantle (7) and tip (12) in e.g. plastic or by punching out plastic. If a transparent material is used, this may also be used for sending light through the pipette, which can help positioning the pipette tip (12) in the right position. A piston (6) inside the pipette (4) can also be made of any material, but TeflonÒ is preferred due to low friction between the inside (31) of the pipette (4) and the piston (6). For movement of the piston (6) inside the pipette (4), the piston (6) is attached to a electromagnet or piezo-element (5).

The pipette (4) allows suction of the islet through the tip (12) which has an inner diameter that is a little larger than the largest cell clusters to be isolated (specifically, for most islet preparations, approximately 250–350 $\mu$m is optimal). The tip (12) of the pipette (4) can be any length, but to ensure that only a small volume of suspension is sucked into the pipette each time cell clusters are isolated, a length of approximately 10 mm is preferred.

Islets are sucked into the pipette when the piston is moved from a first position, where the piston is moved as far as possible into the pipette mantle, outwards to a second position. By performing the outward movement of the piston in small steps, many islets can be sucked into the pipette, before the content inside the pipette is transferred to the second container, for example a culture flask.

Alternatively, only one islet is sucked into the pipette and transported to the second container. This method is slower but avoids clogging inside the pipette.

Figure 4:
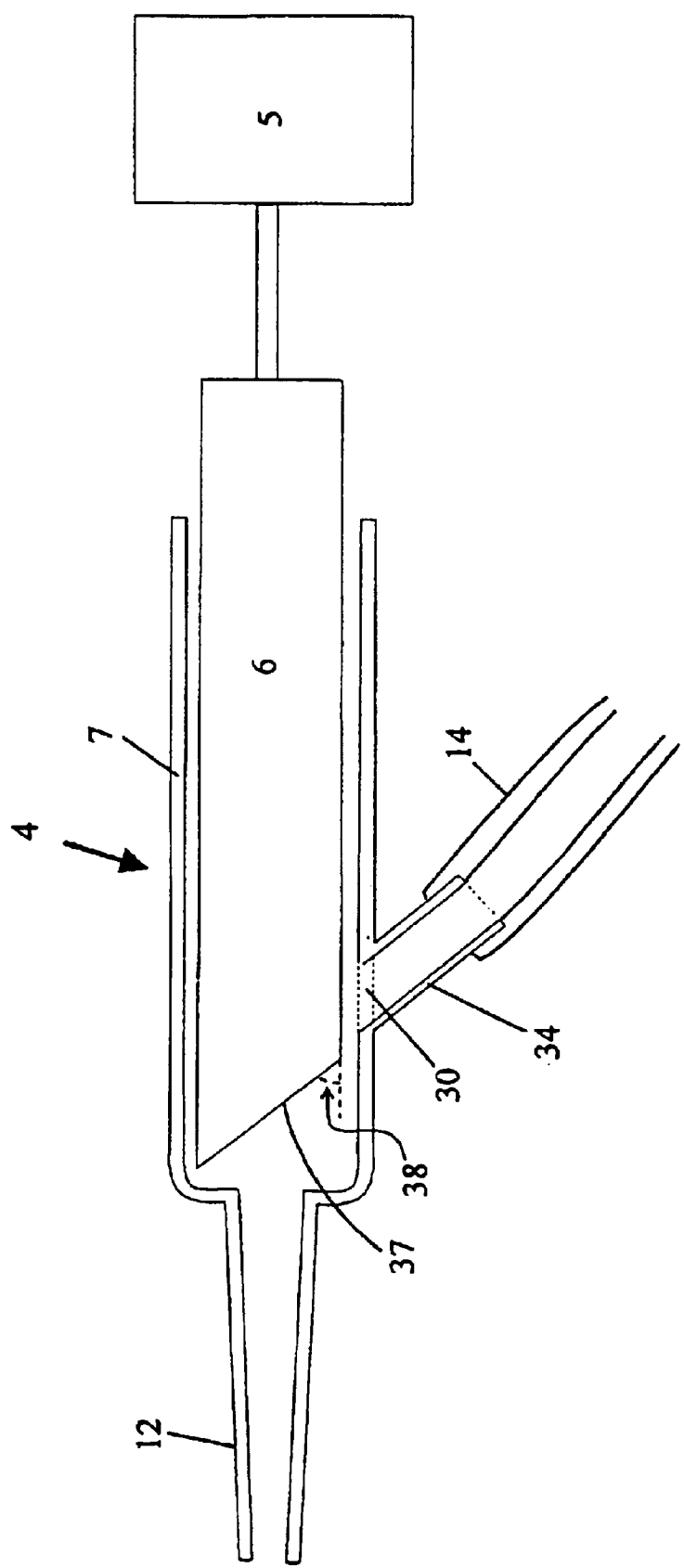
FIG. 4. Pipette model 2: Flow-through pipette without continuous transfer.

FIG. 4 shows pipette model 2, which is a flow-through pipette without continuous transfer. In this embodiment of the invention, the pipette (4) is equipped with a hole for outlet (30) and a short side tube (34) for connection of a transport tube (14) to the pipette (4). The front end (37) of the piston (6) is cut-off with an angle (38) with respect to the moving direction of the piston (6), for example 45°. For movement of the piston (6) inside the pipette (4), the piston (6) is attached to a electromagnet or piezoelement (5).

When the piston (6) is in the first position, where it is fully inserted into the pipette mantle (7), the outlet (30) is closed, so that there is no flow-connection from the pipette tip (12) to the outlet (30). When the piston (6) is moved back from the first position, the outlet (30) is opened and, due to the lower pressure in the transport tube (14), a continuous suction occurs, sucking the islets into the pipette (4) and further through the outlet into the transport tube (14).

Figure 5:
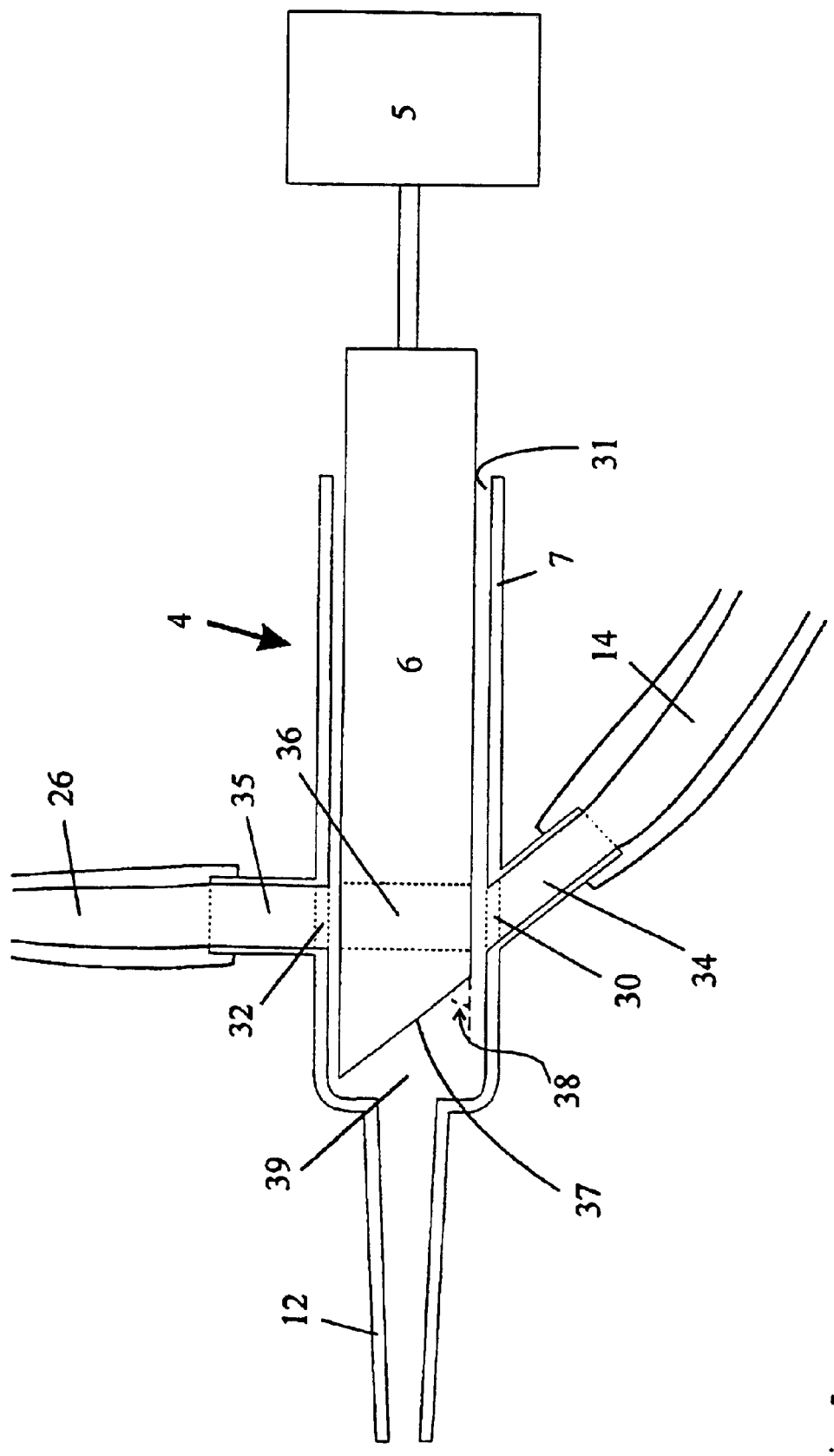
FIG. 5. Pipette model 3: Flow-through pipette with continuous transfer

FIG. 5 shows pipette model 3, which is a flow-through pipette with continuous transfer. In this embodiment of the invention, the mantle (7) of the pipette comprises a hole for inlet (32) and a hole for outlet (30) of fluid. The inlet side tubing (35) is connected via a tubing (26) to a source for culture medium and the outlet side tubing (34) is connected to the transport tube (14).

The piston (6) has a transversal channel (36), the diameter of which is similar to the inner diameter of the holes (30 and 32).

In the first position, where the piston (6) is fully inserted into the pipette (4), fluid flows from the inlet (30), via the channel (36) in the piston (6), through the outlet (30) into the transport tube (14). In a second position, where the piston (6) is moved in an outward direction from the pipette, the piston closes the inlet (32), now allowing a flow from the tip (12) to the pipette-chamber (39) and through the outlet (30) into the transport tube (14).

The piston (6) is connected to a moving device (5). The connection also hinders rotation of the piston (6) in order to keep the channel (36) in the right position relatively to the inlet (32) and outlet (32) securing a correct flow.

Alternatively, the piston (6), instead of having a transverse channel (36), may be shaped with a circular notch allowing fluid to run around the piston from the inlet (32) to the outlet (30).

Figure 6B:
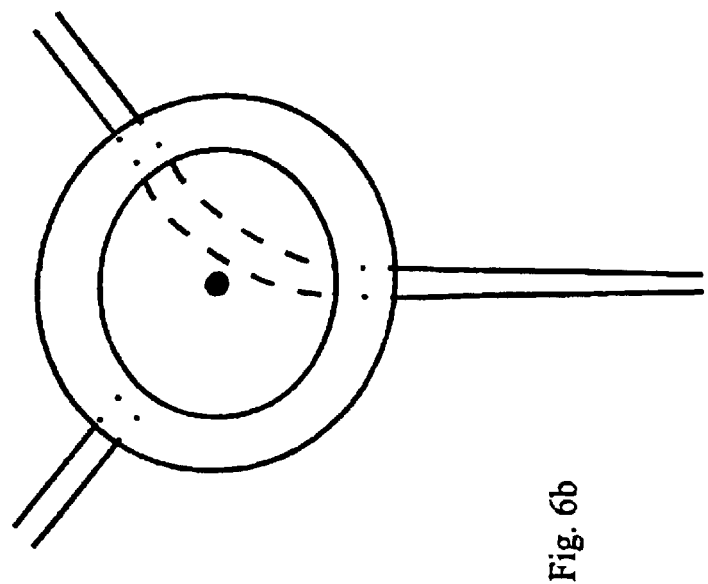
FIGS. 6*a*, 6*b*, and 6*c*. Pipette model 4: Flow-through pipette with continuous transfer.
Figure 6A:
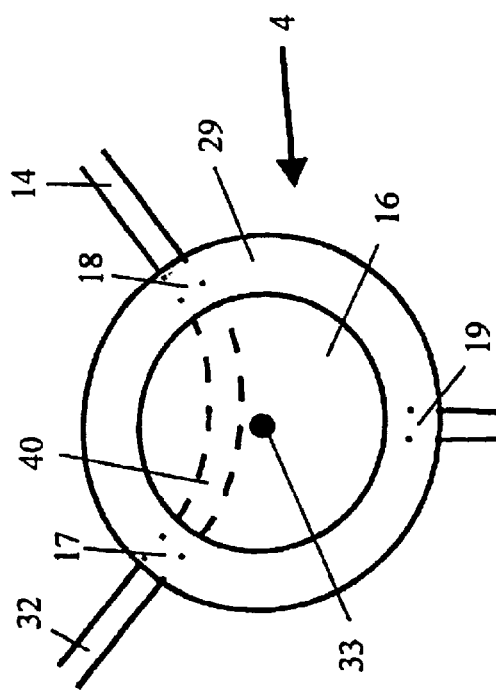
Figure 6C:
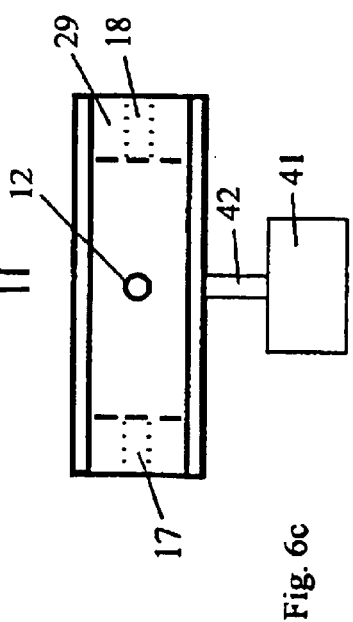

FIG. 6 shows pipette model 4, which is a flow-through pipette with continuous transfer. In this embodiment of the invention, the pipette (4) consists of a cylindrical mantle (29) containing a cylindrical core (16). A projection of it is shown in FIG. 6c. The core (16) can be turned stepwise inside the mantle (29) by a turning device (41), for example an electrical motor or a piezo-unit, which is connected to the core (16) via a turning axle (42).

This pipette (4), as well, ensures fast pipetting and flow-through for transfer of the cell clusters from the pipette tip (12) to the transport tube (14). The core (16) and the mantle (29) can be made of any suitable material, e.g. metal or plastic. For the purpose of supervising the process, it is preferable that the material is transparent The mantle (29) is constructed with three holes (17, 18, 19) pointing towards the centre (33) of the pipette core (16). The holes (17, 18, 19) are positioned with a mutual angular distance of 120º.

The core (16) is constructed with an internal channel (40). The channel (40) has approximately the same diameter as the diameter of the holes (17, 18, 19). The core (16) can be positioned such that it connects two of the three holes, for example the inlet (17) and the outlet (18). In this position, there is a flow of culture medium from a medium supply connected to the inlet (32) through the core channel (40) to the transport tube (14).

In the second position, as shown in FIG. 6b, which is a 120º turn of the core (16), a connection between the pipette tip (12) and the transport tube (14) is established to suck islets through the internal core channel (40) into the transport tube (14).

The turning of the core is fast, so that only a small volume of medium is sucked into the tip (12) and the channel (40) together with the islet.

The apparatus I may be equipped with any type of pipette suitable for sucking in islets. Thus, pipettes based on the well known Pelletier-principle can be mounted as well. A pipette of this type allows for a transfer of a limited number of clusters per handling and the pipette needs to move out of the solution to expel the islets. This pipette is ideal for transfer of a single cell cluster in a small volume to a defined location, e.g. a well-plate, but neither the Pelletier principle nor a pipette as model I is fast enough to ensure fast isolation of a large number of islets.

The tip of the pipettes (12) is important since it directs the flow and supports the cell cluster during the transfer from the bottom of the petri dish (3) to the pipette core. The pipette tip (12) can be either straight (as the type shown in FIGS. 3–6) or bend. The very end of the tip can be cut transversely (as in FIGS. 3–6) or be grinded In the first container, the medium can be illuminated by light coming in from any position. However, for most products in fluid, it is preferable that the light is coming in horizontally. This can be ensured either by flat-fibre optic light or, when using petri dishes, from fibre optic ring lights. These are commercially available. It is important that the voltage frequency does not result in interference with the voltage frequence/shutter speed of the camera. Therefore, DC lamps are preferable.

The visual identification can be performed at all possible wavelengths and in cases, where the islets/cell clusters are subjected to antibodies or other substances for the purpose of identification and/or analysis, fluorescence techniques may be involved.

Figure 7:
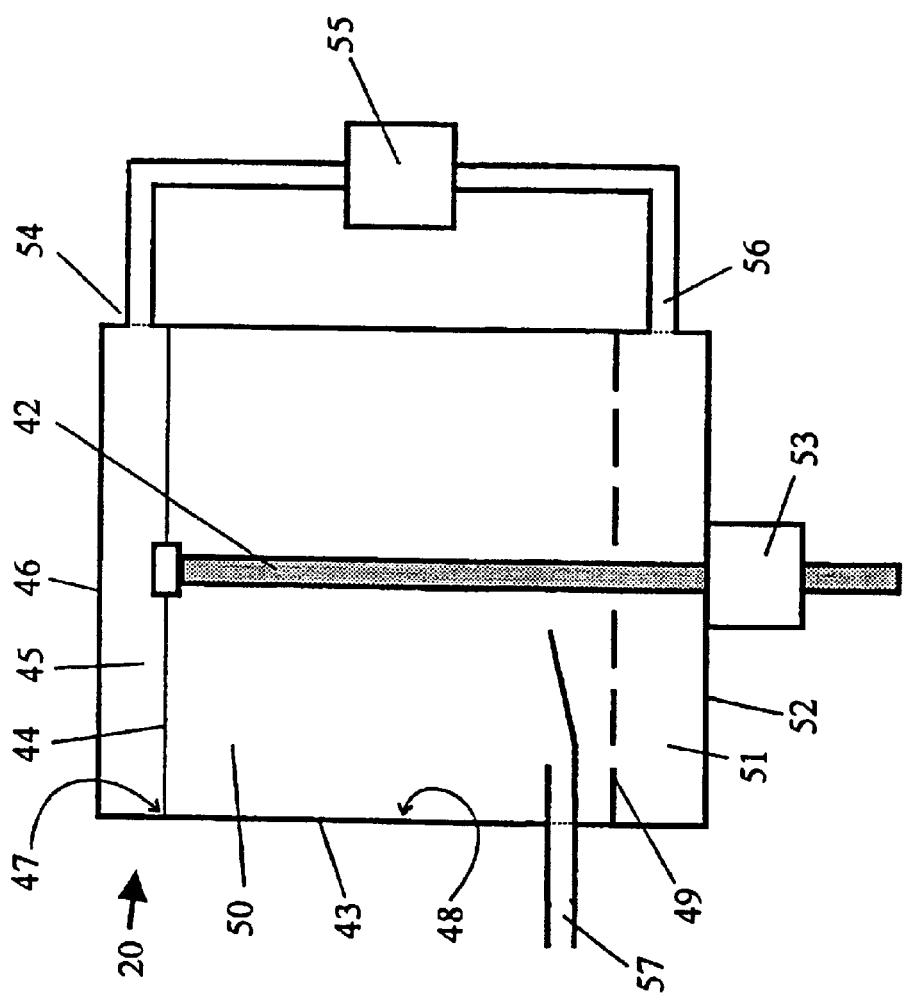
FIG. 7. Reservoir for the tissue suspension.

FIG. 7 shows a possible reservoir (20) for the tissue suspension. The particles of interest will sediment in the solution of the reservoir (20) if special precautions are not undertaken. The velocity by which they sediment depends on characteristics of both the solution and of the particles in solution. E.g. the presence of exocrine tissue influences the sedimentation of the islets.

Two requirements should be fulfilled for successful presentation of the tissue suspension to the camera (1) of the apparatus. Namely first, that the solution is homogenous and second, that the concentration of particles in solution is optimal. These parameters need to be controlled when using either of the apparatus (I or II) presented. e.g. to ensure optimal isolation, the tissue should be loaded to the bottom of the petri dish in a way that displays the tissue in a homogenous pattern and without being too diluted or too concentrated. As part of the invention, a reservoir was developed to fulfill these requirements. Other reservoir types are, however, also applicable.

The special design of the apparatus enables the operator to easily control the homogeneity and the concentration of particles without manual intervention. Eventually the reservoir (20) can be controlled by the computer (2) monitoring the petri dish (3) (model 1) or tube (21) (in model 2). Thus, if the computer (2) detects that the particle concentration or homogeneity is not optimal, the computer (2) can adjust both parameters automatically by build-in routines in the computer program.

The reservoir (20) consists of a mantle (43) that can have any form but for islet isolation, a cylindrical form is preferable. Inside the reservoir (20), a first liquid permeable membrane (44) can be moved up and down along an axle (42) in the cylinder. The first membrane is permeable to the liquid but hinders the particles in the solution to flow through the membrane (44). The rim (47) of the first membrane (44) is tight against the inner wall (48) of the cylindrical mantle (43), which also hinders the cells to escape into the first volume (45) of the reservoir (20). The first volume is the volume between the first membrane (44) and the upper wall (46). At the lower part of the a, cylinder, a second liquid permeable membrane (49) is mounted. Thus, the cylinder now consists of three volumes: the first volume (45) between the first membrane and the upper wall, a second volume (50) between the membranes, and a third volume (51) between the second membrane and the lower wall (52) of the reservoir (20).

The size of the second volume (50) can be changed by movement of the first membrane (44). When the first membrane is moved downwards, the particle concentration in this decreasing volume increases, because the particles are confined in this second volume (50). The movement of the first membrane is enabled by a moving device (53), e.g. a computer controlled electrical motor in connection with the axle. The total volume in the reservoir (20), which is the sum of the first, the second and the third volume, thus is constant.

There is a continuous flow of fluid via tubings from the first volume (45) through an outlet (54), a computer controlled pump (55), and an inlet (56) to the third volume (51). The steady flow of the medium through the second membrane (49) prevents the particles in the second volume (50) from sedimenting on the second membrane (49). The homogeneity of the suspension can be changed by altering the pump pressure at the pump (55), thus changing the flow through the second membrane (49). If necessary, the fluid need not be re-circulating as indicated at FIG. 7 but instead continuous removal, and application, of fluid may be instituted.

The particles in the medium in the reservoir (20) are gradually extracted from the reservoir (20) via a feeding tube (57). The flow through this feeding tube (57) is controlled by the computer, e.g. by comprising a valve. The depletion of solution evoked by the extraction of fluid and particles through the feeding tube (57) and out of the reservoir (20) is prevented by loading (not shown at FIG. 7) of a similar volume of fluid into the reservoir (20).

The reservoir can be cooled down, e.g. by cooling tubings from a water bath.

Description of the Features of the Apparatus

The software is not part of the invention per se. The combination of the apparatus and the designed software ensures the following main features of the entire equipment. The aim has been to develop an equipment that 1. can isolate islets with a high capacity and optimal quality, 2. saves time, 3. is easy to operate, 4. can quantify size and shape of the islets, S. can select subgroups of islets, 6. can calculate islet quality score, 7. can isolate under sterile conditions, 8. potentially isolates islets from any species including human islets.

The apparatus is controlled by software installed on a computer, for example a personal computer (PC). Detailed description of soft-codes is not given here but the main features are outlined below since they throw light on the functional capacities of the invention.

In general, the part of the program capable of identifying the islets is based on algorithms. The program is designed to work under user platforms as for example Windows 98 or Windows NT.

Data obtained from the camera (1) are in the computer used for identification of particles and for further processing by algorithms. The algorithms are based on data of the islet as size, form (e.g. circularity), contrast, intensity, border. A fuzy-logic feature enables the program to learn to recognize particles with special features.

It is possible for the operator to modify the algorithms without the need of detailed knowledge on software. This feature is of special importance if the apparatus is to be working with different particles. To optimize the identification of particles with special patterns and to ensure identical outcome from different units or sets of the apparatus, the algorithms can be exchanged between different computers, eventually as part of a neural network.

The invention includes presentation of the suspension imaged by the camera, where the current view of the camera can be shown on a monitor. Islets fulfilling the criteria as set in the algorithms are identified by the program and marked on the screen. The program can combine single area scans so that a larger area can be displayed on the screen, for example the whole petri dish.

Islet Isolation and Documentation

Operation modes: 1. manual, 2. assisted manual, and 3. automatic operation. In the manual mode, the operator can mark visually identified particles and let the apparatus memorize the islet location for subsequent or immediate isolation. In the assisted manual operation (verification before isolation), the apparatus identifies the particles (according to the set of algorithms used) and marks them on the monitor to aid the operator, if the operator wants tight control with the isolation process. The operator can thus verify the identification before isolation and has the opportunity to unmark unwanted particles before isolation. In the automatic mode, the apparatus quickly identifies (according to the set of algorithms used) and isolates the islets without operator intervention. In apparatus I, all three operation modes are possible, while in apparatus II, only the automatic operation is usable.

Scanning modes: 1. Full scan of the dish before isolation or 2. Scan and isolate within the current image. The apparatus can either scan the whole petri dish and subsequently isolate the islets or it can isolate the islets consecutively after scanning a part of the dish. This feature can be used in apparatus I only.

Selection of islets: Enables the operator to automatically select islets based on fulfilment of predetermined criteria set in the algorithms. The selection criteria can be for example size, form and/or quality. The program can also be set to isolate a preset number of islets with certain characteristics (e.g. the thirty islets of the best quality). This feature can be used in apparatus I only. The selection feature is of importance for the outcome of the subsequent experiments since variation in these parameters may produce large variations in the results obtained from the subsequent experiments.

Data-handling: To improve the digestion and isolation process, it is important to monitor and document physical parameters as e.g. the quality and yield of isolated islets. The program is designed to display and save data on the quantity and quality of the isolated islet size (mean, maximum/minimum), form, volume, colour. A quality score is calculated for each islet and can be displayed on the screen. The mean of the quality score obtained on the particular day of isolation can be saved to file and the information used for later comparisons and statistics. These data are important in order to be able to compare results from different experiments.

Process-handling

Autocalibration, Autostart, and Autoclean. These features are routines in the program of the computer and ensure that the isolation process to a large extent is independent of the operator. In apparatus I, the autocalibration feature include autofocussing and check of the correct position of the pipette tip in the x-y-z plane. The correct positioning of the pipette tip in the z-plane in apparatus I, is secured by manual or computer-controlled adjustments. The Autostart feature will ensure automatic filling of the pipette and tubes. The Autoclean procedure includes routines for cleaning and eventually sterilisation after the isolation is finished (by sucking in e.g. ethanol into the pipette and tubings). This feature will also be operative in case of clotting of the tubings or pipette. E.g. in case the pipette in model 1 is clotted by a tissue clump, the pipette will move out of the petri dish and expel fluid and the move into the petri dish again.

Automatic feeding and filling of petri dishes under the camera is implemented to ensure operator independency.

An automatic check of the quality of the light and of the homogeneity and particle concentration is continuously performed. To ensure optimal circumstances for the isolation process, the computer will analyse the camera data to monitor the quality of the light and the homogeneity and concentration of particles. These parameters can be controlled in the reservoir (FIG. 7). The computer also monitors, via sensors, the suction pressure in the pipette outlet, pump pressure in the reservoir and the temperature in the petri dish and reservoir.

The operator can monitor the isolation process since the program displays the number of the current petri dish processed, residual volume in reservoir, and elapsed time. On the screen the position of the pipette and camera is shown continuously by calibrated coordinates. These can be used for location/relocation purposes, e.g. when performing visual scans.

Additional Documentary Data

Key parameters (as the algorithms applied on that particular isolation, time and date, operator identification, time used for isolation, quantity and quality of the isolated islets) can be saved to file. Comments made by the operator can be written to file. The difference between the identified and isolated number of islets can be calculated. This is of importance for statistics and as information for the operator on the efficacy of the algorithms applied.

The program enables the operator to take snap-shots of the screen (and save these to file) and to perform measurements of e.g. length of islets and calculation of area and estimated volume of marked single islets.

Environment and Hardware

Several units can be coupled to the same computer, which helps speeding up the processing of large amounts of tissue suspension and to keep costs down and save space in a crowded laboratory. As computer, a standard PC with low cost graphics card can be used. The light in the pipette tip secures localization of the tip near the isolate, where it is advantageous to have a transparent pipette mantle and tip for transferring light to the very tip. A gassed hood can be placed over the petri dish or the whole equipment can be placed in a hood, which facilitates exposure of the media to special gas, e.g. for maintaining pH in the medium. The apparatus can operate at low temperature. The low temperature secures low activity of enzymatic processes, which is of importance for protecting the islets from the effects of residual collagenase and harmful enzymes diffusing in the media.

List of Numbers 1. camera
2. computer
3. first container, petri dish
4. pipette
5. piston moving electrical motor or piezo unit
6. piston
7. pipette mantle
8. transport stage
9. transport tube
10. second container, culture flask
11. suction device
12. capillary end section, pipette tip
13. volume around pipette tip
14. transport tube
15. pipette system
16. core, pipette model 4
17. hole inlet, pipette model 4
18. hole for outlet pipette model 4
19. hole for tip pipette model 4
20. reservoir
21. trasparent section of first container
22. first transport section of first container, silicone tubing
23. micro pump or valve
24. side tubing
25. second transport section of first container, silicone tubing
26. waste container
27. further tube
28. mantle of pipette model 4
29. outlet
30. inside of mantle
31. inlet
32. centre of pipette model 4
33. outlet side tubing
34. inlet side tubing
35. channel in piston
36. inclined front end of piston
37. angle between front end of piston and direction of piston movement
38. pipette chamber
39. channel in core of pipette model 4
40. turning device
41. turning axle
42. mantle of reservoir
43. first membrane
44. first volume
45. upper wall of reservoir
46. rim of first membrane
47. inner wall of mantle of reservoir
48. second membrane
49. second volume
50. third volume
51. upper wall of reservoir
52. moving device
53. outlet
54. pump
55. inlet
56. feeding tube

REFERENCES

Brunicardi F C, Suh E, Kleinman R, et al: Selective photodynamic laser treatment of dispersed pancreatic tissue for islet isolation. Transplant.Proc. 24:2796–2797,1992

Buitrago A, Gylfe E, Henriksson C, et al: Rapid isolation of pancreatic islets from collagenase digested pancreas by sedimentation through Percol at unit gravity. Biochem-.Biophys.Res.Commun. 79:823–828,1977

Davies J E, James R F, London N. J., et al: Optimization of the magnetic field used for immunomagnetic islet purification. Transplantation 59:767–771,1995

Fetterhoff T J, Wile K J, Coffing D, et al: Quantitation of isolated pancreatic islets using imaging technology. Transplant.Proc. 26:3351,1994

Gotoh M, Maki T, Satomi S, et al: Reproducible high yield of rat islets by stationary in vitro digestion following pancreatic ductal or portal venous collagenase injection. Transplantation 43:725–730,1987

Gray, B. and Baird, M. K. Isolation of cells from organ tissue using sonication. PCT/US96/05667(C12N 5/00,5/06). 1996. 96. Patent Gray D W, Gohde W, Carter N, et al: Separation of pancreatic islets by fluorescence-activated cell sorting. Diabetes 38:133–135,1989

Hara Y, Taniguchi H, Yarnashiro Y, et al: An improved method for the isolation of islets from the rat pancreas. Exp.Clin.Endocrinol. 91:171–175,1988

Jindal R M, McShane P, Gray D, et al: Isolation and purification of pancreatic islets by fluorescence activated cell sorter. TransplantProc. 26:653,1994

Lacy P E, Kostianovsky M: Method for the isolation of intact islets of Langerhans from the rat pancreas. Diabetes 16:35–39,1967

Lake S P, Anderson J, Chamberlain J, et al: Bovine serum albumin density gradient isolation of rat pancreatic islets. Transplantation 43:805–808,1987

Lake S P, Basset P D, Larkin A, et al: Large-scale purification of human islets utilizing discontinous albumin gradient on IBM 2991 Cell Separator. Diabetes 38:143–145, 1989

Lake S P, James R F L, Anderson J. et al: TransplantProc. 18:1817,1986

Lakey J R, Warnock G L, Brierton M, et al: Development of an automated computer-controlled islet isolation system. Cell Transplant. 6:47–57,1997

Langley, R. W. Method and apparatus for purifying islets of Langerhans. 93301790.7(0561549A2). 1993. 93. Patent Merchant F A, Diller K R, Aggarwal S J, et al: Viability analysis of cryopreserved rat pancreatic islets using laser scanning confocal microscopy. Cryobiology. 33:236–252, 1996

Marchetti P, Finke E H, Gerasirnidi-Vazeou A, et al: Automated large-scale isolation, in vitro function and xenotransplantation of porcine islets of Langerhans. Transplantation 52:209–213,1991

Loir M: Trout Sertoli and Leydig cells: isolation, separation, and culture. Gamete Res. 20:437–458,1988

Lubbe F H, Rossi G, Zaalberg O B: Isolation of antibody-forming cells by using cluster formation in combination with velocity sedimentation. J.Immunol.Methods 12:131–140,1976

Nandigala P, Chen T H, Yang C, et al: Immunomagnetic isolation of islets from the rat pancreas. Biotechnol.Prog. 13:844–848,1997

Olack B, Swanson C, McLear M, et al: Islet purification using Euro-Ficoll gradients. Transplant.Proc. 23:774–776,1991

Prevost P, Rolland E, Veriot C, et al: Large-scale isolation of porcine pancreatic islets: significant improvement of the process. Transplant.Proc. 27:3396–3398,1995

Ricordi C: Quantitative and qualitative standards for islet isolation assessment in humans and large mammals. Pancreas 6:242–244,1991

Ricordi C, Finke E H, Dye E S, et al: Automated isolation of mouse pancreatic islets. Transplantation 46:455–457, 1988

Ricordi C, Finke E H, Lacy P E: A method for the mass isolation of islets from the adult pig pancreas. Diabetes 35:649–653,1986

Ricordi C, Gray D W, Hering B J, et al: Islet isolation assessment in man and large animals. Acta Diabetol.Lat. 27:185–195,1990

Ricordi C, Lacy P E, Finke E H, et al: Automated method for isolation of human pancreatic islets. Diabetes 37:413–420,1988

Sharp, D. W., Lacy, P. E., Finke, E. H., and Poteat, T. J. Islet isolation process. 86300858.7(0191613A2).1986.86. Patent Shibata A, Ludvigsen C W J, Naber S P, et al: Standardization fo a digestion-filtration method for isolation of pancreatic islets. Diabetes 25:667–672,1976

Stegemann J P, O'Neil J J, Nicholson D T, et al: Improved assessment of isolated islet tissue volume using digital image analysis. Cell Transplant. 7:469–478,1998

Stegemann J P, O'Neil J J, Nicholson D T, et al: Automated counting and sizing of isolated porcine islets using digital image analysis. Transplant.Proc. 29:2272–2273,1997

Teruya M, Idezuki Y, Bandai Y, et al: New digestion chamber for the automated isolation method of pancreatic islets. Transplant.Proc. 26:2279–2280,1994

Tze W I, Wong F C, Tingle A J: The use of hypaque-ficoll in the isolation of pancreatic islets in rats. Transplantation 22:201–205,1976

Vandewalle B, Douillard C, Kerr C J, et al: Human pancreatic islet quality control: easy assessment of metabolic functions. Exp.Clin.Endocrinol.Diabetes 107:214–219, 1999

Wile K J, Schwartzkopf W, Olsen M, et al: Differentiation of free and embedded porcine pancreatic islets using a novel automated image analysis algorithm. Transplant.Proc. 29:1974,1997

What is claimed is:

1. Apparatus for automatic isolation of particles, comprising:

a reservoir containing a solution with particles;

a first container into which an amount of said solution with said particles is fed from said reservoir;

a second container for accumulation of specific ones of said particles;

a capillary tube device for picking out one of said specific particles from said first container and for transporting said specific particles to said second container;

a computer system;

a camera system for recording images of said particles and transferring those images digitally to said computer system; and a computer program implemented in said computer system, which computer program evaluates said images, identifies and selects said specific particle from said images by predetermined parameters, protocols physical/chemical and/or biochemical characteristics of said specific particle, and controls said picking out and said transport of said specific particle;

said first container including a first tube with a transparent section, said first tube being connected to and communicating with said reservoir;

said second container including a side-tube;

said first tube having an internal flow of said solution with particles from said reservoir;

said camera system recording images of said particles in said transparent section;

said capillary tube device comprising a micro pump, which micro pump is connected to said first tube, and which micro pump by signal from said computer system picks out said specific particle from said solution by pumping a small portion of said solution containing said specific particle into said side-tube.

2. Apparatus for automatic isolation of particles, comprising:

a reservoir containing a solution with particles;

a first container into which an amount of said solution with said particles is fed from said reservoir;

a second container for accumulation of specific ones of said particles;

a capillary tube device for picking out one of said specific particles from said first container and for transporting said specific particles to said second container, wherein said capillary tube device comprises a transparent section with an inner cross section larger than said specific particles;

a computer system;

a camera system for recording images of said particles in said first container and in said transparent section and transferring those images digitally to said computer system, where the field of view of the camera contains said first container and said transparent section; and a computer program implemented in said computer system, which computer program evaluates said images, identifies and selects said specific particle from said images by predetermined parameters, protocols physical/chemical and/or biochemical characteristics of said specific particle, and controls said picking out and said transport of said specific particle.

3. Apparatus for automatic isolation of particles, comprising:

a reservoir containing a solution with particles;

a first container into which an amount of said solution with said particles is fed from said reservoir;

a second container for accumulation of specific ones of said particles;

a capillary tube device for picking out one of said specific particles from said first container and for transporting said specific particles to said second container, wherein said capillary tube device comprises a transparent section with an inner cross section larger than said specific particles;

a computer system;

a camera system for recording images of said particles in said first container and said transparent section and transferring those images digitally to said computer system, where the field of view of the camera contains said first container and said transparent section; and a computer program implemented in said computer system, which computer program evaluates said images, identifies and selects said specific particle from said images by predetermined parameters, protocols physical/chemical and/or biochemical characteristics of said specific particle, and controls said picking out and said transport of said specific particle;

said capillary tube device comprising:

a pipette with a pipette chamber and a transparent capillary end section for picking out said specific particle from said first container, said pipette chamber comprising a piston inside said pipette that is moved by a moving device, which moving device is controlled by said computer system with said computer program, wherein the volume of the pipette chamber is changed by the movement of said piston; and a transport stage with motors for moving said pipette to the position of said specific particle and, after picking up said specific particle, transporting said specific particle to said second container, which transport stage is controlled by said computer with said computer program.

4. Apparatus for automatic isolation of particles, comprising:

a reservoir containing a solution with particles;

a first container into which an amount of said solution with said particles is fed from said reservoir;

a second container for accumulation of specific ones of said particles;

a capillary tube device for picking out one of said specific particles from said first container and for transporting said specific particles to said second container, wherein said capillary tube device comprises a transparent section with an inner cross section larger than said specific particles;

a computer system; and a camera system for recording images of said particles in said first container and in said transparent section and transferring those images digitally to said computer system, where the field of view of the camera contains said first container and said transparent section;

a computer program implemented in said computer system, which computer program evaluates said images, identifies and selects said specific particle from said images by predetermined parameters, protocols physical/chemical and/or biochemical characteristics of said specific particle, and controls said picking out and said transport of said specific particle;

said capillary tube device comprising:

a pipette with a pipette container and a transparent capillary end section for picking out said specific particle from said first container by sucking out of said first container a small portion of solution that contains said particle;

a transport tube connected to said pipette for transporting said specific particle from said capillary end section to said second container;

a piston inside said pipette chamber, wherein the volume of the pipette chamber is changed by the movement of said piston;

a moving device to move said piston between a first and a second position, which moving device is controlled by said computer system with said computer program determining the first and second position, where said piston in the first position inhibits, and in the second position establishes, a connection between the capillary end section and the transport tube;

a suction device creating a lower pressure in said second container and in said transport tube, such that, when said piston is in said second position, solution is transported from said capillary end section into said transport tube; and a transport stage with motors for moving said pipette with said capillary end section to the position of said selected specific particle in said solution in said first container, which transport stage is controlled by said computer with said computer program.

5. Apparatus for automatic isolation of particles, comprising:

a reservoir containing a solution with particles;

a first container into which an amount of said solution with said particles is fed from said reservoir;

a second container for accumulation of specific ones of said particles;

a capillary tube device for picking out one of said specific particles from said first container and for transporting said specific particles to said second container;

a computer system;

a camera system for recording images of said particles and transferring those images digitally to said computer system; and a computer program implemented in said computer system, which computer program evaluates said images, identifies and selects said specific particle from said images by predetermined parameters, protocols physical/chemical and/or biochemical characteristics of said specific particle, and controls said picking out and said transport of said specific particle; said capillary tube device comprising:

a pipette with a transparent capillary end section for picking out said specific particle from said first container by sucking out of said first container a small portion of solution that contains said particle;

a transport tube connected to said pipette for transporting said specific particle from said capillary end section to said second container;

a supplier tube connected to said pipette;

a piston inside said pipette;

a moving device to move said piston between a first and a second position, which moving device is controlled by said computer system with said computer program determining said first and said second positions, where said piston in said second position establishes a connection between the capillary end section and the transport tube and inhibits a connection between the supplier tube and the transport tube;

a hollow channel in said piston, which channel, when said piston is in said first position, inhibits the connection between said capillary end section and one of said transport tube and said supplier tube but connects said supplier tube with said transport tube such that fluid can flow from said supplier tube to said transport tube;

a suction device creating a lower pressure in said second container and in said transport tube, such that, when said piston is in said first position, solution is transported from said supplier tube to said transport tube, and when said piston is in said second position, solution is transported from said capillary end section into said transport tube; and a transport stage with motors for moving said pipette with said capillary end section to the position of said selected specific particle in said solution in said first container, which transport stage is controlled by said computer with said computer program.

6. Apparatus for automatic isolation or particles, comprising:

a reservoir containing a solution with particles;

a first container into which an amount of said solution with said particles is fed from said reservoir;

a second container for accumulation of specific ones of said particles;

a capillary tube device for picking out one of said specific particles from said first container and for transporting said specific particles to said second container, wherein said capillary tube device comprises a transparent section with an inner cross section larger than said specific particles;

a computer system;

a camera system for recording images of said particles in the first container and said transparent section and transferring those images digitally to said computer system, where the field of view of the camera contains said first container and said transparent section; and a computer program implemented in said computer system, which computer program evaluates said images, identifies mid selects said specific particle from said images by predetermined parameters, protocols physical/chemical and/or biochemical characteristics of said specific particle, and controls said picking out and said transport of said specific particle; said capillary tube device comprising:

a pipette with a pipette container and a transparent capillary end section for picking out said specific particle from said first container by sucking out of said first container a small portion of solution that contains said particle;

a transport tube connected to said pipette for transporting said specific particle from said capillary end section to said second container;

a supplier tube connected to said pipette;

a piston inside said pipette chamber, wherein the volume of the pipette chamber is changed by the movement of said piston;

a moving device to move said piston between a first and a second position, which moving device is controlled by said computer system with said computer program determining said first and said second position, where said piston in said second position establishes a connection between the capillary end section and the transport tube and inhibits the connection between the stippler tube and the transport tube;

a hollow channel in said piston, which channel, when said piston is in said first position, inhibits the connection between said capillary end section and one of said transport tube and said supplier tube and connects said supplier tube with said transport tube such that fluid can flow from said supplier tube to said transport tube;

a suction device creating a lower pressure in said second container and in said transport tube, such that, when said piston is in said first position, solution is transported from said supplier tube to said transport tube, and when said piston is in said second position, solution is transported from said capillary end section into said transport tube; and a transport stage with motors for moving said pipette with said capillary end section to the position of said selected specific particle in said solution in said first container, which transport stage is controlled by said computer with said computer program.

7. Apparatus for automatic isolation of particles, comprising:

a reservoir containing a solution with particles;

a first container into which an amount of said solution with said particles is fed from said reservoir;

a second container for accumulation of specific ones of said particles;

a capillary tube device for picking out one of said specific particles from said first container and for transporting said specific particles to said second container;

a computer system;

a camera system for recording images of said particles and transferring those images digitally to said computer system; and a computer program implemented in said computer system, which computer program evaluates said images, identifies and selects said specific particle from said images by predetermined parameters, protocols physical/chemical and/or biochemical characteristics of said specific particle, and controls said picking out and said transport of said specific particle; said capillary tube device comprising:

a pipette with a transparent capillary end section for picking out said specific particle from said first container by sucking out of said first container a small portion of solution that contains said particle;

a transport tube connected to said pipette for transporting said specific particle from said capillary end section to said second container;

a supplier tube connected to said pipette;

a turnable cylindrical core inside said pipette;

a turning device to turn said turnable cylindrical core between a first and a second position, which turning device is controlled by said computer system with said computer program determining said first and said second position;

a hollow channel in said turnable cylindrical core, which channel, when said turnable cylindrical core is in said first position, connects said supplier tube with said transport tube and closes a connection to said capillary end section, and which channel, when said turnable cylindrical core is in said second position, connects said capillary end section with said transport tube and closes said supplier tube;

a suction device creating a lower pressure in said second container and in said transport tube, so that, when said turnable cylindrical core is in said first position, solution is transported from said supplier tube to said transport tube, and when said turnable cylindrical core is in said second position, solution is transported from said capillary end section into said transport tube; and a transport stage with motors for moving said pipette with said capillary end section to the position of said selected specific particle in said solution in said first container, which transport stage is controlled by said computer with said computer program.

8. Apparatus according to any one of the claims 1–7, wherein said reservoir defines an internal volume, said apparatus further comprising:

a cylindrical mantle surrounding the solution, which cylindrical mantle has an upper wall, a lower wall and a curved wall;

first and second liquid permeable membranes that divide the internal volume of the reservoir into first, second, and third volumes that are mutually distinct, said first volume being between said first membrane and said upper wall of the mantle, said second volume being between said first and second membranes, and said third volume being between said second membrane and said lower wall of the mantle;

an axle at least partly inside the reservoir, which axle is situated along the center of said cylindrical mantle, along which axle, said first membrane is movable;

a moving device for controlled movement of the first membrane along the axle;

a pump with a tubing, which pump pumps suspension from said first volume through said tubing into said third volume; and a feeding tube to feed suspension from said reservoir to said first container.

9. The apparatus according to any one of the claims 1–7 wherein the particles are selected from the group consisting of specific cell types, cell clusters obtained by treating organic tissue with dissociating methods, and Islets of Langerhans.

* * * * *